United States Patent [19]

Neilan et al.

[11] Patent Number: 4,826,983
[45] Date of Patent: May 2, 1989

[54] N-2,2-DIMETHYL-2-(2-HYDROXY-ALKYL-PHENYL) HETEROCYCLES AND STABILIZED COMPOSITIONS

[75] Inventors: James P. Neilan, Bear, Del.; John F. Stephen, West Chester, Pa.

[73] Assignee: ICI Americas Inc., Wilmington, Del.

[21] Appl. No.: 121,427

[22] Filed: Nov. 16, 1987

Related U.S. Application Data

[63] Continuation of Ser. No. 800,288, Nov. 21, 1985, abandoned.

[51] Int. Cl.$^4$ ............................................. G07D 251/00
[52] U.S. Cl. ...................................... 544/221; 524/101
[58] Field of Search .......................... 524/101; 544/221

[56]  References Cited

U.S. PATENT DOCUMENTS

| | | | |
|---|---|---|---|
| 3,531,483 | 9/1970 | Gilles | 524/101 |
| 3,723,427 | 3/1973 | Susi | 524/101 |
| 4,033,937 | 7/1977 | Argabright et al. | 544/221 |
| 4,461,862 | 7/1984 | Eigenmann | 524/101 |
| 4,520,151 | 5/1985 | Chaser | 524/101 |
| 4,569,736 | 2/1986 | Kosegaki et al. | 524/101 |

Primary Examiner—John Kight
Assistant Examiner—Kriellion Morgan

[57]  ABSTRACT

Novel hindered hydroxyphenyl alkyl isocyanurates are provided which are useful as stabilizers of resins made from at least one ethylenically unsaturated monomer.

1 Claim, No Drawings

N-2,2-DIMETHYL-2-(2-HYDROXY-ALKYLPHENYL) HETEROCYCLES AND STABILIZED COMPOSITIONS

This is a continuation of co-pending application Ser. No. 800,288 filed on Nov. 21, 1985, now abandoned.

The present invention is directed to compounds having alkylhydroxyphenol groups bonded to a heterocyclic nitrogen atom via a dimethylethyl group and stabilized polymer resins containing them. It is also directed to resins containing the novel stabilizers and co-stabilizing antioxidant sulfur-containing compounds.

The compounds of this invention contain alkylhydroxyphenyl groups bonded to a heterocyclic nitrogen atom through a dimethylethyl bridging group. At least one nitrogen atom is located between two carbonyl or thiocarbonyl groups in the ring. The heterocyclic nucleus of the present compounds will contain one or more imidocarbonyl or imidothiocarbonyl groups. The compounds of the present invention are represented by the general formula:

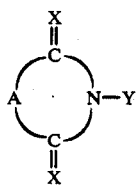

where Y is

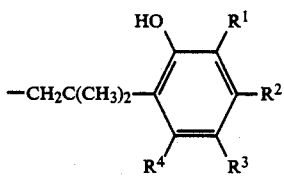

wherein $R^1$, $R^2$, $R^3$, $R^4$ are independently selected from H or alkyl groups having 1–12 carbon atoms. X is oxygen or sulfur, and A is a bivalent molecular grouping having a chain of 2–3 atoms. The bivalent radical A may be a hydrocarbon radical, such as alkylene having 2–3C atoms or ortho phenylene, or may contain at least one C atom and one or two atoms selected from N, O, S in functional groups such as >NH, >C=S, and >C=O. Heterocyclic compounds containing nitrogen atoms for substitution with alkylhydroxyphenyl groups include isocyanuric acid, uric acid, hydantoins, alloxan, uracil, thymine, barbituric acid, succinimide and maleimide and derivatives thereof, phthalimide and derivatives thereof.

A preferred class of compounds are derivatives of s-triazine-2,4,6-trione (isocyanurates), having the following general formula:

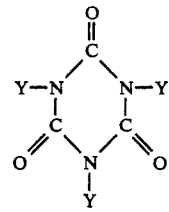

where Y is as defined above.

It is known that organic materials deteriorate upon exposure to air. The compounds of this invention are stabilizers for such organic materials normally subject to oxidative deterioration. Materials which are thus stabilized include synthetic organic polymeric substances such as vinyl resins formed from the polymerization of vinyl halides or from the copolymerization of vinyl halides with unsaturated polymerizable compounds, for example vinylesters, β-unsaturated ketones, β-unsaturated aldehydes, and unsaturated hydrocarbons such as butadienes and styrene; poly-α-olefins such as polyethylene, polypropylene, polybutylene, and the like including copolymers of poly-α-olefins, polyurethanes and polyamides such as polyhexamethylene adipamide and polycaprolactam; polyesters such as polyethylene terephthalates; polycarbonate; polyacetals; polystyrene; polyethyleneoxide; polyisoprene; polybutadiene and copolymers such as those of high impact polystyrene containing copolymers of butadiene and styrene and those formed by the copolymerization of acrylonitrile, butadiene and/or styrene.

In general one or more of the stabilizers of the present invention are employed in amounts based on the total weight of the resin of from about 0.005 to about 5% by weight of the composition to be stabilized. A particularly advantageous range of the present stabilizers is from about 0.05% to about 2%. The preferred range is particularly effective in polyolefins such as polypropylene.

The compounds of the invention may be incorporated in the polymer substrate during the usual processing operations, for example, by milling or extrusion. The stabilized polymer can be fabricated into films, fibers, filaments, hollowspheres and the like. The heat stabilizing properties of these compounds advantageously stabilize the polymer against degradation during such processing at the high temperatures generally employed.

The stabilizers employed in this invention can also be used in combination with other stabilizers or additives. In general these co-stabilizers are represented by those having the following general formula: [RO-CO(C$_m$H$_{2m}$)CH$_2$]$_2$S wherein R is an alkyl group having from 6–24 carbon atoms; and m is an interger from 1–6. Especially useful co-stabilizers are dilauryl-β-thiodipropionate and distearyl-β-thiodipropionate (DSTDP). These co-stabilizers are used in an amount ranging from 0.01–2% by weight of the organic material and preferably from 0.1–1% by weight.

The stabilizers described in this invention can also be used in combination with di- and tri-alkyl and alkylphenyl phosphites such as tris-nonylphenyl phosphite, tris(2,4-di-tert-butylphenyl)phosphite, bis(2,4-di-t-butylphenyl)pentaerythritol diphosphite, tetrakis(2,4-di-t-butylphenyl)-4,4'-biphenylene diphosphonite, and distearyl pentaerythritol diphosphite.

Other antioxidants, antiozonants, thermal stabilizers, ultraviolet light absorbers, coloring materials, dyes, pigments, metal chelating agents, etc., may also be used in the compositions in combination with the stabilizers of the invention.

The compounds of the invention may be synthesized by addition of trimethallylisocyanurate (TMI), prepared according to a procedure outlined in U.S. Pat. No. 3,075,979, to the appropriate phenol in the presence of a suitable Lewis acid catalyst such as BF$_3$Et$_2$O. A preferred process involves reacting trimethallylisocyanurate with a 3-100 mol excess of an alkyl phenol such as 2,4-xylenol, p-cresol, 4-ethyl phenol, 4-sec butyl phenol, in the presence of BF$_3$Et$_2$O catalyst at 50°-150° C.

Similar hindered hydroxyphenyl isocyanate derivatives are described in U.S. Pat. Nos. 3,531,483 and 3,723,427 wherein the hydroxyphenyl group is linked directly to the isocyanurate nitrogen through a methylene group at the meta and para positions.

The following examples serve to illustrate but not limit the invention wherein all proportions expressed are by weight unless otherwise specified.

EXAMPLE 1

1,3,5-Tris[2,2-dimethyl-2-(2-hydroxy-3,5-dimethylphenyl)ethyl]-s-triazine-2,4,6-(1H,3H,5H)trione Trimethallyl isocyanurate (10 g, 0.034 mole) and 2,4-xylenol (25 g, 0.205 mole) are stirred under nitrogen in a 50 ml 3-neck flask. To this suspension is added 0.25 ml BF$_3$.Et$_2$O. The reaction is heated at 100° C. for 16 hours. At this time, a white precipitate has formed. The product is separated from unreacted xylenol by filtration. The solids are washed with petroleum ether (BP 35°-50° C.) to yield 23 g white solid containing a small amount of 2,4-xylenol. The product can be further purified by dissolving in 150-200 ml acetone and pouring into 400 ml hexane. Concentration of the resulting solution to 300 ml results in isolation of 14.1 g (66%) of product, mp 210°-211° C.

Calc. for C$_{39}$H$_{51}$N$_3$O$_6$: C, 71.19; H, 7.83; N, 6.39
Found: C, 71.18; H, 7.95; N, 6.22.

EXAMPLE 2

1,3,5-Tris[2,2-dimethyl-2-(2-hydroxy-5-methylphenyl)ethyl]-s-triazine-2,4,6-(1H,3H,5H)trione TMI (10 g, 0.034 mole) and p-cresol (70 g, 0.66 mole) are stirred under N$_2$ in a 100 ml 3-neck flask. To this suspension is added 0.25 ml BF$_3$.Et$_2$O. The reaction is heated for 16 hours at 100° C. The resulting white precipitate is recovered by filtration and washed with petroleum ether to give 21.4 g white solid, contaminated with p-cresol. The product can be purified by recrystallization from acetonitrile to give 16.8 g (80.3%) of product, mp 248°-250° C.

Calc. for C$_{36}$H$_{45}$N$_3$O$_6$: C, 70.21; H, 7.38; N, 6.82
Found: C, 69.83; H, 7.44; N, 6.53.

EXAMPLE 3

1,3,5-Tris[2,2-dimethyl-2-(2-hydroxy-5-methyl-3-t-butylphenyl)ethyl]-s-triazine-2,4,6-(1H,3H,5H)trione To a 50 ml 3-neck round bottom flask is charged 2 g product of Example 2 in 10 ml nitrobenzene. 0.1 ml H$_2$SO$_4$ is added and isobutylene is bubbled through the solution while warming to 90° C. After TLC shows the reaction to be complete, the mixture is diluted with an equal volume of ethyl acetate and washed 2 times with 50 ml 5% sodium bicarbonate. The organic layer is dried and concentrated in vacuo. The residue is purified by dry column chromatography (Et$_2$O/hexane) to yield 1.3 g of product, mp 215°-217° C.

Calc. for C$_{48}$H$_{69}$N$_3$O$_6$: C, 73.51; H, 8.89; N, 5.36
Found: C, 73.12; H, 8.94; N, 5.04.

EXAMPLE 4

1,3,5-Tris[2,2-dimethyl-2-(2-hydroxy-5-ethylphenyl)ethyl]-s-triazine-2,4,6-(1H,3H,5H)trione To a 100 ml 3-neck round bottom flask is charged 50 g 4-ethylphenol. The contents are warmed to 60° C. and 10 g TMI is added, followed by 0.2 ml BF$_3$.Et$_2$O. The contents are heated to 100°-120° C. for 16 hours. The resulting solids are isolated by filtration, yielding 15.6 g of white solid containing unreacted ethylphenol. The solids are recrystallized from acetone to yield 4.9 g of product, mp 202°-205° C.

Calc. for C$_{39}$H$_{51}$N$_3$O$_6$: C, 71.19; H, 4.83; N, 6.39
Found: C, 71.01; H, 4.63; N, 6.27.

EXAMPLE 5

1,3,5-Tris[2,2-dimethyl-2-(2-hydroxy-5-sec-butylphenyl)ethyl]-s-triazine-2,4,6-(1H,3H,5H)trione To a 100 3-neck round bottom flask is charged 50 g 4-sec-butylphenol. The contents are heated to a molten state and 10 g TMI is added, followed by 0.2 ml BF$_3$.Et$_2$O. The contents are warmed to 100°-120° C. for 16 hours. The excess 4-sec-butylphenol is removed by vacuum stripping. The pot residue is transferred to 350 ml hexane while stirring. The resulting white powder is collected by filtration yielding 19.8 g white powder. The product can be purified by recrystallization from hexane/acetione to yield 6.1 g white solid, m.p. 185° C.

EXAMPLE 6

1,3,5-Tris[2,2-dimethyl-2-(2-hydroxy-5-ethyl-3-t-butylphenyl)ethyl]-s-triazine-2,4,6-(1H,3H,5H)trione To a 100 ml 3-neck round bottom flask is charged 8.9 g product of Example 4 in 30 ml toluene. To this is added 0.8 g p-toluenesulfonic acid. Isobutylene is passed through the solution while warming to 90° C. When TLC shows the reaction to be complete, the contents are diluted with an equal volume of ethyl acetate and washed 2 times with 50 ml of 5% sodium bicarbonate. The organic layer is dried, and stripped under vacuum. The residue is purified by dry column chromatography to give 3.3 g white solids. Further purification by precipitation from a water/methanol solution gives 2.4 g of product.

Calc. for C$_{57}$H$_{87}$N$_3$O$_6$: C, 75.19; H, 9.65; N, 4.62
Found: C, 75.06; H, 9.55; N, 4.75.

EXAMPLE 7

1,3,5-Tris[2,2-dimethyl-2-(2-hydroxy-4-methylphenyl)ethyl]-s-triazine-2,4,6-(1H,3H,5H)trione To a 100 ml 3-neck round bottom flask is charged 62 g m-cresol and 10 g TMI. To this is added 0.2 ml BF$_3$.Et$_2$O. The contents are stirred at 100° C. under N$_2$ for 16 hours. The contents are cooled and solids isolated by filtration and washing with petroleum ether to give 13.2 g of white solid. The product can be purified by recrystallization from acetonitrile to yield 7.9 g product.

Calc. for C$_{36}$H$_{45}$N$_3$O$_6$: C, 70.21; H, 7.38; N, 6.82
Found: C, 70.03; H, 7.74; N, 6.89.

EXAMPLE 8

N,N'-Bis 2,2-dimethyl-2-(2-hydroxy-3,5-dimethylphenyl)ethyl-5,5-dimethylhydantoin (A) Prep of N,N'-bismethallyl-5,5-dimethylhydantoin: In a 100 ml three necked flask is placed 10 g (0.055 mole) of N-methallyl-5,5-dimethylhydantoin in 100 ml DMF under nitrogen. The solution is cooled to 15° C. and 2.7 g of sodium hydride/mineral oil is added. The reaction is stirred for 2 hours at 15° C. and then warmed to 25° C. Methallyl chloride (5.1 g, 0.56 mole) is added dropwise over 10 minutes, keeping the temperature at 30° C. The reaction is stirred overnight, then poured into 200 ml water, extracted with 2×100 ml ether and dried over magnesium sulfate. After removing the ether in vacuo, the residue is distilled under vacuum (BP 100°–105° C. @0.3 mm Hg) to give 11.9 g N,N'bismethallyl-5,5-dimethyl hydantoin.

(B) Prep of N,N'-bis 2,2-dimethallyl-2-(2-hydroxy-3,5-dimethylphenyl)ethyl-5,5-dimethyl hydantoin: In a 100 ml three-necked flask is placed 10 g N,N'-bismethallyl hydantoin in 65 ml 2,4-xylenol. To this solution is added 0.5 ml $BF_3EtO_2$ and the reaction is warmed to 100° C. for 16 hours. The excess xylenol is removed by distillation and the residue purified by dry column chromatography to give the product as a white solid, mp 150°–152° C.

Calc. for $C_{29}H_{40}N_2O_4$: C, 72.45; H, 8.40; N, 5.83 Found: C, 72.71; H, 8.46; N, 5.90.

EXAMPLE 9

1,3-Bis-2,2-dimethyl-2-(2-hydroxy-3,5-dimethylphenyl)ethylpyrimidine-2,4,6-(1H,3H,5H)trione (A) Prep of bis-methallylbarbiturate: Barbituric acid (11.4 g, 0.1 mole), triethylamine (32 g, 0.32 mole) and o-dichlorobenzene (80 ml) are heated at reflux for 16 hours. The triethylamine hydrochloride is filtered off from the hot reaction mass and washed with ether. The ether washings are combined with the mother liquor, washed 2 times with 100 ml water, dried over magnesium sulfate and concentrated in vacuo to produce crude bis-methallyl barbiturate.

(B) Prep of 1,3-bis-2,2-dimethyl-2-(2-hydroxy-3,5-dimethylphenyl)ethylpyrimidine-2,4,6-(1H,3H,5H)trione: Bis-methallyl barbiturate prepared in part A is treated with a ten fold excess of 2,4-xylenol in the presence of a catalytic amount of $BF_3EtO_2$. The reaction contents are heated to 100° C. for 16 hours. The excess xylenol is removed by vacuum distillation and the product isolated by dry column chromatography.

EXAMPLE 10

The following data show the stabilization imparted to organic polymers on addition of compound in the examples.

This example shows the usefulness of the invention for stabilization of polypropylene. The stabilizers were incorporated into Profax 6301 ™ polypropylene resin by solvent blending (methylene chloride) followed by extrusion at 200° C. Twenty-five mil plaques were prepared by compression molding at 6,000 psi and 188° C. Samples were tested in a forced draft oven at 150° C. Failure was determined when the first signs of decomposition were observed. Tests were run in quadruplicate and an average value was determined. Results are shown in Table I.

TABLE I

| Stabilizer | Concentration (%) | Hours to Failure |
| --- | --- | --- |
| none | — | 24 |
| Ex. 1 | 0.10 | 510 |
| Ex. 2 | 0.10 | 126 |
| Ex. 3 | 0.10 | 672 |
| Ex. 4 | 0.10 | 150 |
| Ex. 5 | 0.10 | 156 |
| Ex. 6 | 0.10 | 72 |
| Ex. 7 | 0.10 | 90 |
| Ex. 1/DSTDP | 0.1/0.25 | 2364 |
| Ex. 2/DSTDP | 0.1/0.25 | 2412 |
| Ex. 3/DSTDP | 0.1/0.25 | 1932 |
| Ex. 4/DSTDP | 0.1/0.25 | 1242 |
| Ex. 5/DSTDP | 0.1/0.25 | 1494 |
| Ex. 6/DSTDP | 0.1/0.25 | 1140 |
| Ex. 7/DSTDP | 0.1/0.25 | 1410 |

EXAMPLE 11

This example shows the usefulness of the invention for stabilization of high impact polystyrene. The stabilizers were incorporated into high impact polystyrene by milling at 188° C. Twenty mil plaques were prepared by compression molding at 6,000 psi and 188° C. Samples were tested in a forced draft oven at 90° C. Failure was determined when cracking was observed after flexing the plaque over a one-inch mandrel. Tests were run in quadruplicate and an average value was determined. Results are shown in Table II.

TABLE II

| Stabilizer | Concentration (%) | Hours to Failure |
| --- | --- | --- |
| none | — | 48 |
| Ex. 1 | 0.10 | 192 |
| Ex. 2 | 0.10 | 72 |
| Ex. 4 | 0.10 | 186 |
| Ex. 5 | 0.10 | 246 |

What is claimed is:

1. A process for preparing a hindered hydroxyalkyl isocyanurate having the formula

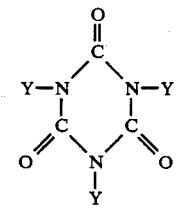

wherein Y is the radical

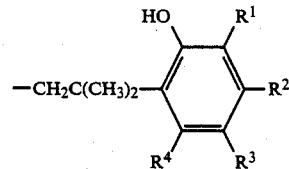

and wherein $R^1$, $R^2$, $R^3$, and $R^4$ are independently hydrogen or hydrocarbon radicals containing 1–12 carbon atoms by reacting trimethallylisocyanurate with a 3–100 mol excess of an alkyl phenol with 0.0–10% $BF_3Et_2O$ at 50°–150° C.

* * * * *